United States Patent [19]

Shim

[11] Patent Number: 4,765,327

[45] Date of Patent: Aug. 23, 1988

[54] CARTRIDGE HUMIDIFIER VENT VALVE

[75] Inventor: Norman Shim, Glenview, Ill.

[73] Assignee: Respiratory Care, Inc., Arlington Heights, Ill.

[21] Appl. No.: 944,393

[22] Filed: Dec. 19, 1986

[51] Int. Cl.⁴ ............... A61M 15/00; A61M 16/00
[52] U.S. Cl. ........................... 128/204.13; 261/142
[58] Field of Search ............. 128/203.27, 204.13, 128/202.22, 203.19; 261/35, 142, 38

[56] References Cited

U.S. PATENT DOCUMENTS

| | | | |
|---|---|---|---|
| 4,051,205 | 9/1977 | Grant | 128/203.27 |
| 4,110,419 | 8/1978 | Miller | 128/203.27 |
| 4,366,105 | 12/1982 | Nowacki | 128/203.27 |
| 4,500,480 | 2/1985 | Cambio | 128/202.22 |
| 4,674,494 | 6/1987 | Wiencek | 128/204.13 |

Primary Examiner—William E. Kamm
Assistant Examiner—George Manuel
Attorney, Agent, or Firm—Donald N. Halgren

[57] ABSTRACT

The present invention comprises a cartridge humidifier assembly having a heating means for humidifying a gas supplied from a source and delivered to a patient. The cartridge humidifier has a cap which defines a chamber with a column. The cap includes a port which receives the gas from a ventilator and a port which permits the discharge of heated humidified gas to the patient. The cap also has a single air-vent port for the venting of air with the water supply from the chamber of cartridge assembly. Water is supplied to the bottom of the cartridge assembly from a one-way conduit in communication with the bottom of the water supply container. A float rises to close off the air-vent when the cartridge assembly is full. The float lowers itself, unblocking the vent to the water bottle supply from the cartridge assembly, as the water level in the cartridge is used up in the humidification process. The float air-vent control is thus automatic, preventing possible overflow or lack of flow of water in the system.

13 Claims, 2 Drawing Sheets

# CARTRIDGE HUMIDIFIER VENT VALVE

BACKGROUND OF THE INVENTION

(1) Field of the Invention

This invention relates generally to humidifier devices and more particularly to disposable humidifier cartridges assemblies which receive water from an adjacent container.

(2) Prior Art

Inhalation therapy generally includes a humidifying means where oxygen, air, other gases which ought to be breathed by a patient, to aid in his respiration, are preferably both heated and humidified under controlled conditions. It is preferred that a sterile liquid be used for the humidification process.

Such inhalation therapy equipment is shown for instance in U.S. Pat. No. 4,110,419, wherein a heated cartridge receives a supply of water from a vented, rigid walled container.

U.S. Pat. No. 4,366,105 shows a humidifier system with a water source feeding a cartridge type heater-humidifier, having a plurality of clamps and check-valves. The clamps must be manually operated and the level of water checked periodically. A further example of the art is shown in U.S. Pat. No. 4,500,480 which shows a pediatric cartridge humidifier having a plurality of conduits disposed between the humidifier and the water supply. The prior art does not permit the cartridge heaters to have automatic shut-off control which is a very desirable feature to minimize the extent of maintenance of such an inhalation system, and to guard against the possiblity of over-flow of the system to the detriment (possible drowning) of the patient. This is of critical significance when the system is in use in a pediatric environment. Baxter Travenol makes an "Optimal" column which uses a pair of manually regulatable conduits from a rigid walled water source, one conduit for supply and the other conduit for venting, in addition to a port to the patient and a port from the gas source.

It is an object of the present invention to provide an inhalation system which is fail-safe in operation. That is, where shut-off is positive and automatic, not needing manual control, which guards against the flooding of the system.

It is yet a further object of the present invention to provide an inhalation system where the water level is constant, a situation, particularly desirable in pediatric use.

BRIEF SUMMARY OF THE INVENTION

An inhalation system having a cartridge type humidifier-heater which receives its water supply from a source such as a bottle. The cartridge hmidifier-heater consists of an aluminum column or canister generally closed at one end. A rolled up piece of absorbent paper or the like is disposed against the inside of the aluminm column to act as a wick. The column has an infundibuliform cap on its open end. The cap has a centrally disposed air-vent shut-off port therethrough. A pair of oxygen ports are disposed on opposite sides of the vent shut-off port, all of the ports having axes that are generally parallel. The centrally disposed vent port has a conically shaped opening on the inwardly directed side of the cap. The distalmost edge of the vent shut-off port is of a sharp configuration. Disposed about the vent port on the inner side of the cap, is a tubular member which extends somewhat inwardly into the column.

A float is disposed from within the column and has a cylindrical shaft element which extends into the tubular element on the inside of the cap. The float embodiment may be comprised of generally three sections. The first section is a generally cylindrically shaped lowermost section which meets a second conically shaped section near its midpoint. An uppermost section of the float comprises the cylindrically shaped shaft which extends into the tubular element disposed about the discharge on the inside of the cap. A soft surface may be disposed on the uppermost distal end of the shaft on the top of the float. Several longitudinally directed baffles are disposed inside of the cap between the elongated tubular element and the outside edge of the cap.

A water-containment bottle, which comprises the water source, may be connected via a one-way conduit at its bottom, to an inlet port arranged through the bottom of the cannister. Water is thus permitted to drain into the cannister through the one-way conduit. A venting conduit is attached to the vent port and to the top of the water containment bottle. As the water level rises within the column from the conduit connecting the bottoms of the cannister and the supply bottle, the float sitting on the bottom of the cannister, is caused to rise. The shaft, comprising the uppermost end of the float, is guided in the tubular element extending inwardly from the cap, until is strikes the sharp circular edge of the opening of the central port. This acts as an air-flow stopper to the water supply bottle and prevents further water from draining therefrom and entering the column, until it is required. The other two oxygen ports disposed within the cap on the top of the cartridge are in respective fluid communication with the ventilator or gas source, and with the patient. Each is also of course in fluid communication within the chamber defined by the column.

As the water is wicked up by the paper wick on the inside of the column, it is heated and passes by evaporation to the air within the column, the water level within the column then drops and hence permits the float to drop as well. Then the air flow being stopped at the opening is no longer prevented from flowing through the vent conduit, and discharge of water from the bottom of the bottle and into the bottom of the cartridge is again permitted until it causes the float to rise and again strike the sharp edge of the orifice in the vent port, preventing further air from flowing to the supply bottle. The generally longitudinally directed baffles direct air coming from the ventilator within the inhalation system to travel longitudally within the chamber and mix and extract moisture from the wick therewithin. The other oxygen port then directs the humidified and heated air to the patient as needed.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENT

Figure 1:
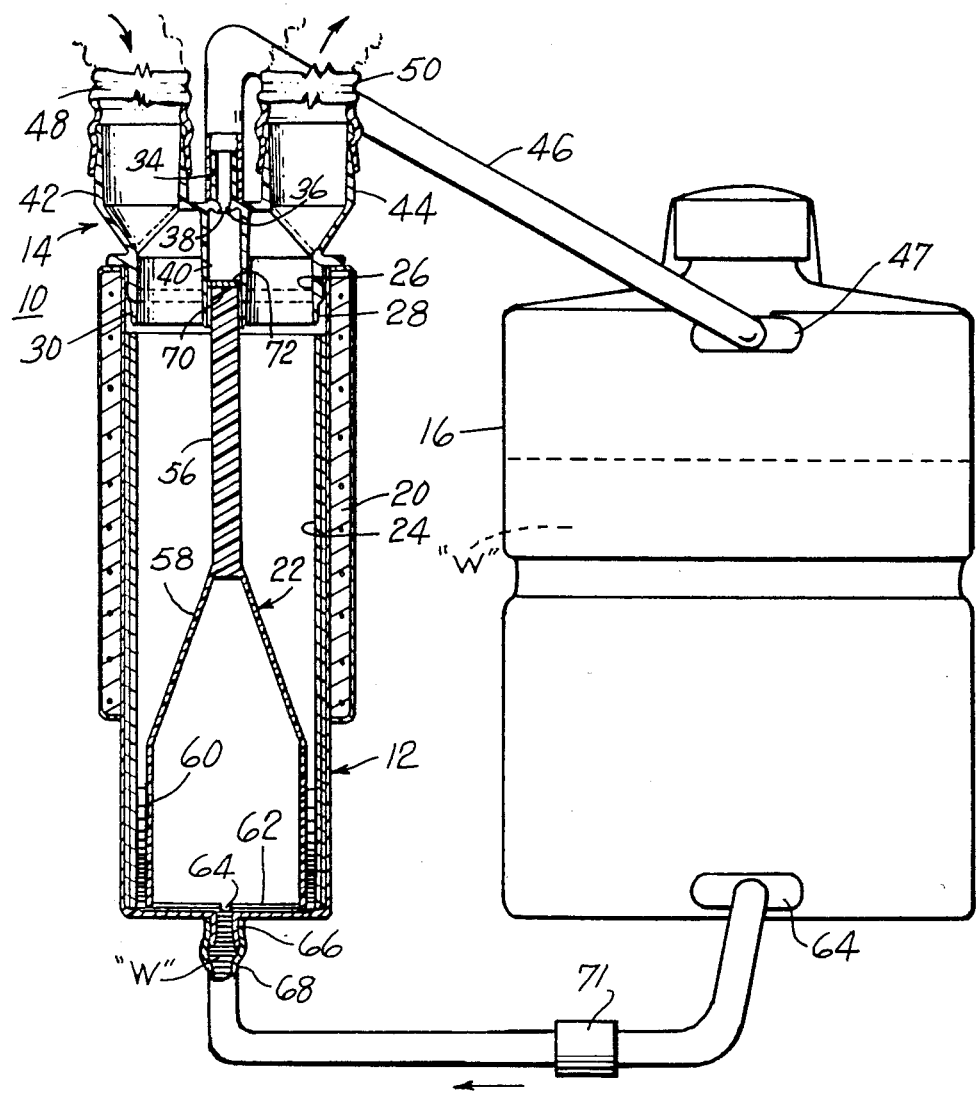
FIG. 1 is a cross sectional view of a canister assembly with very little water therein, constructed in accordance with the principles of this invention.

Referring now to the drawings in detail, and particularly to FIG. 1, there is shown an inhalation humidifier cartridge assembly 10 comprising a column 12, an infundibuliform top cap 14, and a water supply source 16 such as a rigid walled water bottle. The column 12, shown here, is enclosed within a supportable heater sleeve 20. The column 12 is generally similar to the column shown in copending commonly assigned U.S. patent application Ser. No. 944,397, entitled Disposable Cartridge Humidifier, incorporated herein by reference.

The cartridge 12 is preferably of cylindrical configuration, and contains a hollow float 22 of generally cylindrical configuration. The inside walls of the column 12 are lined with a wick 24 which may be made from a water absorbent material such as paper, and wound several layers thick thereinside. The top cap 14 is arranged to fit snugly into the opening of the column 12. The cap 14 has an inside annular flange 26 and may have an annular recess 28 therearound. An O-ring 30 may mate in the annular recess 28 so as to effect a peripheral seal between the flange 26 and the inside wall of the column 12.

Figure 2:
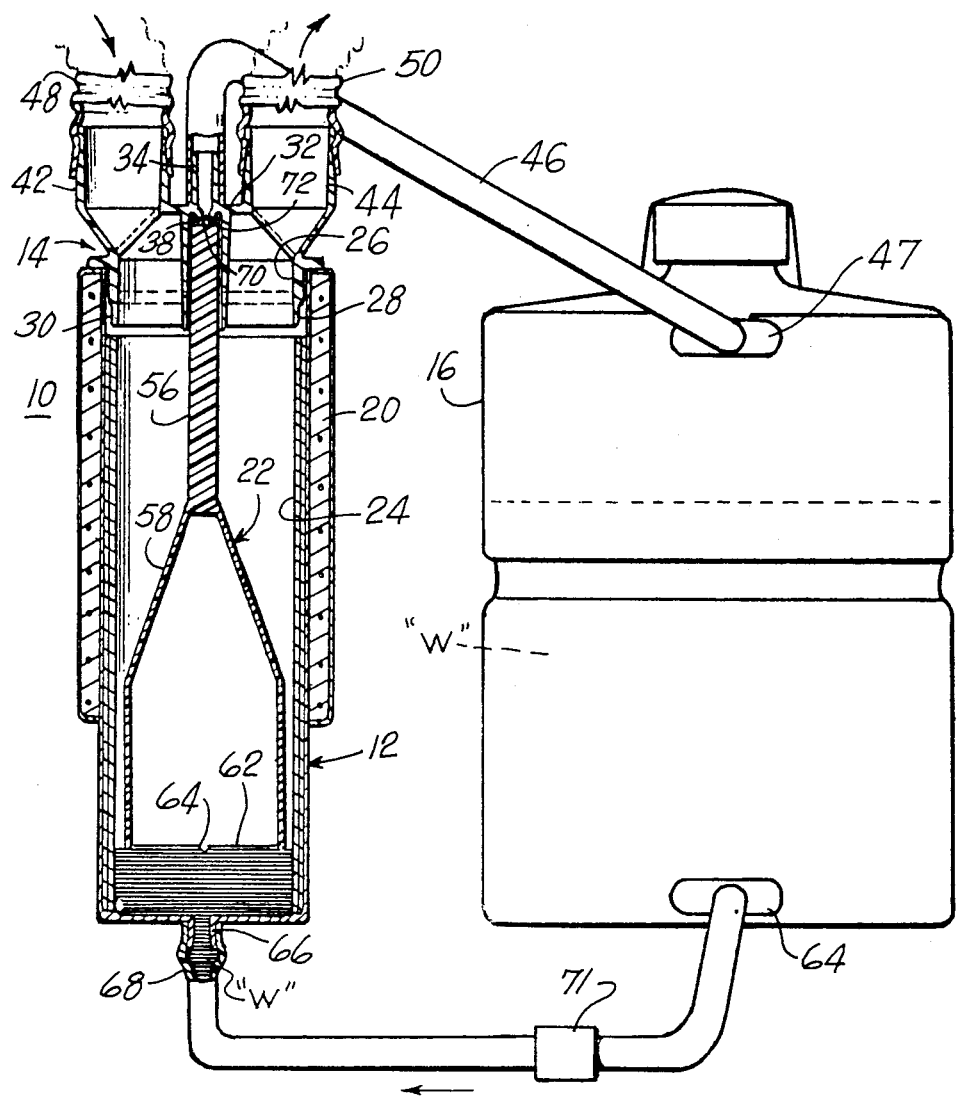
FIG. 2 is a view similar to FIG. 1, the cannister having its full capacity of water.

The top cap 14 has a generally planar uppermost portion 32 as shown most clearly in in the aforementioned commonly assigned copending application. A centrally disposed channel 34 extends through the top 32 of the cap 14. The central channel 34 has a reduced opening 36 axially disposed through the cap top 32. A downwardly extending lip 38 forms a sharp edged annular ring on the inwardly directed side of the top surface 32 of the cap 14. A tubular member 40 extends inwardly from the inside of the top surface 32 of the cap 14 which is also in fluid communication with the central channel 34 and the opening 36. A pair of gas ports 42 and 44 are shown in FIGS. 1 and 2, which ports 42 and 44 are preferably arranged in the cap 14 and are generally parallel with the longitudinal axis of the column 12. The two ports 42 and 44 are importantly in fluid communication with the chamber defined by the top cap 14, and the chamber defined by the interior of the column 12. It is significant that only two gas ports 48 and 50, and the vent channel 34 are in communication with the column 12 and the patient.

An air-vent conduit 46 is attached to the distalmost end of the central channel 34 and a port 47 near the top of water supply container 16. A pair of conduits 48 and 50 mate with the distal lips of the oxygen ports 42 and 44 respectively. The conduits 48 and 50 are directed to the patient and to a ventilator respectively, not shown. The ventilator supplies the air (a gas flow) to the apparatus 10, under pressure, which air is heated and humidified within the apparatus. The air is supplied at a constant (positive) base pressure, and is intermittently increased to supply pulses of pressurized air to the patient to facilitate his breathing.

A pair of baffles, not shown, extend inwardly from the inside peripheral surface of the top cap 14 partially dividing the chamber therein in half. The baffles are utilized to conduct the gas flow into the chamber defined by the column 12 from its proper port 42 or 44, and effectuate more efficient moist heat transfer from the wick 24 to the gas for the patient.

The hollow float exposed within the column 12 is of generally cylindrical configuration. The uppermost half portion of the hollow float 22 comprises a shaft 56. The lowermost proximal portion of the shaft 56 may be attached to an intermediate segment 58 of the float 22. The lowermost portion of the intermediate segment 58 comprises a cylindrical shaped portion 60. The intermediate segment 58 may be cone shaped. The cylindrical portion 60 of the hollow float 22 is preferably open at is lowermost end 62. The lowermost end 62 may have a plurality of feet 64 thereon. The feet 64 are arranged to co-act with the bottom of the column 12 to minimize the surface tension therewith and prevent the float 22 from "sticking" to the bottom of the column 12 has a water inlet port 66 thereon which is connected to a water supply conduit 68. The other end of the water conduit 68 is attached to a discharge port 69 on the bottom of the water supply bottle 16. A one-way check valve 71 prevents water from flowing backwardly from the column cannister 12 to the bottle 16.

The upper or distalmost end of the shaft 56 on the top end of the hollow float 22 extends into the tubular member 40 in a sliding relationship. The diameter of the lower most portion 60 of the hollow float 22 is of such dimensions so as to permit non-contacting relationship between it and the wick 24 which lines the inside wall of the column 12. The same is true between the shaft 56 and the tubular member 40. The shaft 56 has a disk like uppermost surface 70 onto which a rubber or rubber-like pad 72 is secured.

During operation of the apparatus 10, when heated humidified air is desired to be discharged to a patient, the air-vent conduit 46 and the water supply conduit 68 are each attached to the top and bottom of the water supply 16, respectively, the lower end of the air-vent conduit 46 also being attached to the central vent port 34. Water is then permitted to enter the chamber defined by the column 12 by passing through the supply conduit 68, the port and then into the chamber of the cannister 12. As the water level in the column 12 rises, as shown in FIG. 2, it causes the hollow float 22 to be lifted upwardly due to the air being trapped within the float itself by the water sealing off the open lowermost end 62 of the hollow float 22". Once a certain amount of water has been passed into the column 12 through the supply conduit 68, the float 22 will rise sufficiently high so that its upper surface 70, having a rubber-like pad thereon is in contact with the sharp annular edge extending downwardly from the orifice 36. The pressure of the pad thereupon shuts off the flow of venting air supply to the top of the bottle 16 automatically, as shown in FIG. 2, until the hollow float 22 has been caused to drop down again within the column 12. This occurs when sufficient water within the chamber of the column 12 has heated and evaporated and has passed out through whichever of the tubular members 48 or 50 goes to the patient. Thereupon passage of water through the supply conduit 68 and air for venting the bottle 16 through the vent conduit 46 and opening 36 may begin anew.

Every time the water level drops due to the quantity of moisture in the heated moist air being discharged out of one of the two ports 48 or 50, the float is thus permitted to automatically lower itself thus opening the only other port in the cap 14, that is, the air-vent port within the cap. By having a constant base pressure within the chamber of the column 12, as supplied by the ventilator, the float is forced into its shut-off position against the ring 38 with force greater than just a buoyancy force.

Thus, it has been shown a novel automatically controllable means for permitting a constant supply of water to be discharged into a humidifying system on an as needed basis which system also permits an automatic shut-off of vent air to the water supply bottle so as to completely preclude the possibility of flooding or detriment to the patient thereby.

I claim:

1. A cartridge type humidifying apparatus for use with a heating means and for receiving water from a supply container, for heating and humidifying a breathable gas to be inhaled by a patient undergoing inhalation therapy, comprising:
   a humidifier column having a top end and a bottom end, said column arranged for the containment of water therein;
   a cap on the top end of said column, said column and said cap defining a chamber for said gas;
   said chamber having a gas delivery port for receipt of gas thereto, a gas discharge port communicable with a patient, and an air-vent port for permitting the flow of air from said column to a water container supply means; and
   a float movably disposed in said column, having an uppershaft portion which is in communication with said air-vent port to act like a valve for controlling the discharge of water from a supply container through a conduit and into a port on the bottom of said column.

2. A cartridge type humidifying apparatus as recited in claim 1, wherein said gas delivery port, said gas discharge port and said air-vent port are all disposed through said cap on said column.

3. A cartridge type humidifying apparatus as recited in claim 1, wherein said air-vent port has a tubular member which extends down into said cartridge, said tubular member acting as a guide means for said upper shaft portion of said float.

4. A cartridge type humidifying apparatus as recited in claim 3, wherein said float has a hollow cylindrically-shaped lower portion which has an open bottom end.

5. A cartridge type humidifying apparatus as recited in claim 3, wherein said upper shaft portion of said float co-acts with said air-vent port to control the flow of air therethrough thereby controlling the air flow to the water supply container, thereby controlling the water flow from the water supply container.

6. A cartridge type humidifying apparatus as recited in claim 3, wherein said upper shaft portion of said float has a layer of soft material on its distalmost end which is contactable with said air-vent port when said cartridge is supplied with water from said supply container to lift said float to close said air-vent port.

7. A cartridge type humidifying apparatus as recited in claim 3, including a wick to aid the humidification of air therein.

8. A cartridge type humidifying apparatus as recited in claim 3, including a one-way valve in said conduit.

9. A cartridge type humidifying apparatus for providing heated and humidified air to a patient, the apparatus comprising:
   a water container supply;
   a column having an upper end and a lower end, said column having means for heating air supplied thereto;
   a cap covering the upper end of said column;
   a wick arranged in said column for wicking water in said cartridge for evaporation into the chamber defined by said cap and said column;
   said cap having a vent port means for transmitting vent air to said water supply from said chamber, a port means for discharging treated air from said chamber to a patient, and a float valve means for regulating the flow of air from said chamber to said water container; and
   a supply conduit from the bottom of said water supply to a port to the bottom of said column to feed water to said column to regulate said float valve.

10. A cartridge type humidifying apparatus as recited in claim 9, where said supply conduit has a one-way valve disposed therein to prevent water flowing the wrong way from said column to said water supply.

11. The method of controlling the flow of water to a cartridge type humidifying apparatus having a column with an upper end and a bottom, a top cap secured to the upper end of said column, a float means movable disposed in said column, an air vent in communication with the water source and a supply conduit from a water source, comprising the steps of:
   supplying water to the column through a conduit from a water source to a port on the bottom of said column; and
   regulating the flow of water from the water source by said float means.

12. The method of claim 11, including the step of:
   moving the float means into engagement with said air vent to stop the flow of water from the water source.

13. The method of claim 12, including the step of:
   moving the float means out of engagement with said air vent to permit the flow of water from the water source.

* * * * *